United States Patent [19]

Baldwin et al.

[11] 3,967,759
[45] July 6, 1976

[54] SYRINGE ASSEMBLY WITH CONTAINED POP-OUT ELASTIC PLUG SEAL

[75] Inventors: Brian E. Baldwin, Wilmette; Edward A. Tischlinger, Plaines, both of Ill.

[73] Assignee: MPL, Inc., Chicago, Ill.

[22] Filed: Mar. 18, 1974

[21] Appl. No.: 451,910

Related U.S. Application Data

[62] Division of Ser. No. 197,845, Nov. 11, 1971, abandoned.

[52] U.S. Cl. .......................... 222/145; 128/218 M; 222/386
[51] Int. Cl.² ........................................ B65D 37/00
[58] Field of Search .......................... 222/145, 386; 128/218 C, 218 D, 218 M, 218 P, 218 PA, 218 R, 272; 128/218 D, 218 M

[56] References Cited
UNITED STATES PATENTS

| | | | |
|---|---|---|---|
| 2,607,341 | 8/1952 | Brown | 128/272 |
| 3,110,309 | 11/1963 | Higgins | 128/218 D |
| 3,345,986 | 10/1967 | Roberts et al. | 222/145 |
| 3,366,286 | 1/1968 | Kloehn | 222/386 |
| 3,417,904 | 12/1968 | McLay | 222/386 |

*Primary Examiner*—Stanley H. Tollberg
*Assistant Examiner*—David A. Scherbel
*Attorney, Agent, or Firm*—Kinzer, Plyer, Dorn & McEachran

[57] ABSTRACT

A prefillable or prefilled syringe having a liquid-containment glass tube body section with thermoplastic resin finger-grip sleeve and noseforming sleeve fit thereon in an interference fit, and with the ends of the glass tube being sealed after filling and preferably prior to assembly of one or both the finger-grip sleeve and the nose-forming sleeve, and a method of assembly thereof, the finger-grip sleeve and the nose-forming sleeve being cam-stretched onto and frictionally retained on and along a glass tube, in the form of a section of die-formed glass tubing. Increase in latitude of operable interference fit and stretch is effected by assembling the finger-grip sleeve and the noseforming sleeve in a heated condition, without requiring heating of the glass tube and its prefilled contents. A preferred embodiment utilizes a pop-out valve plug seal in the nose end of the glass tube, with a plunger piston at the opposite end, for sealed prefilled containment of a liquid drug or other chemical agent in the glass tube.

57 Claims, 11 Drawing Figures

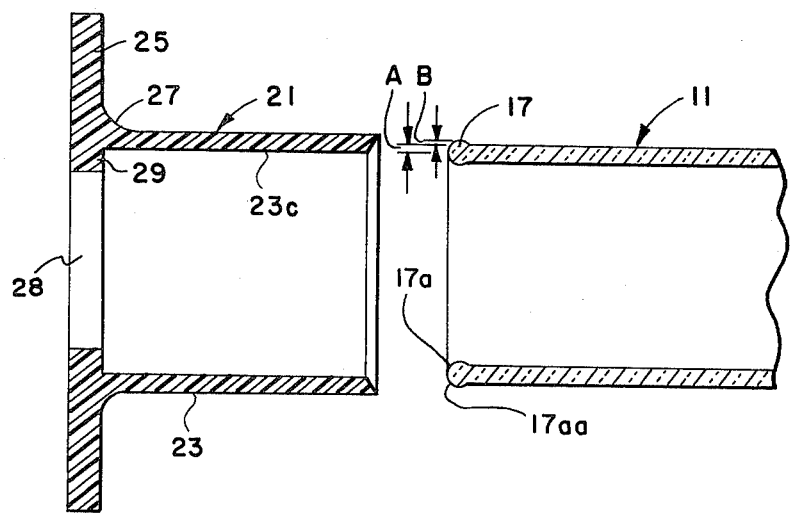
FIG. 5
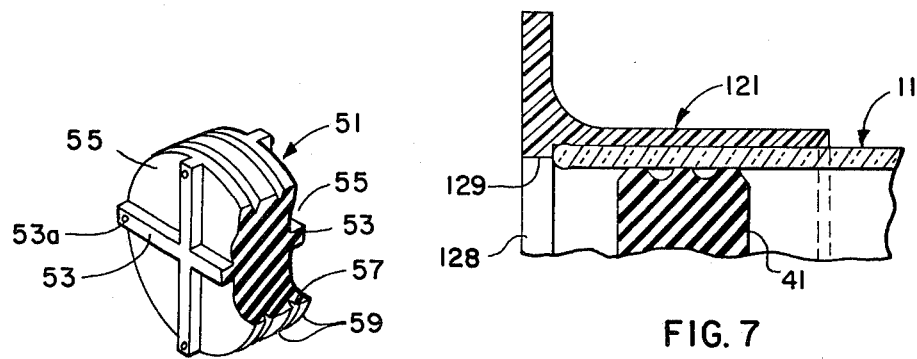
FIG. 6
FIG. 7
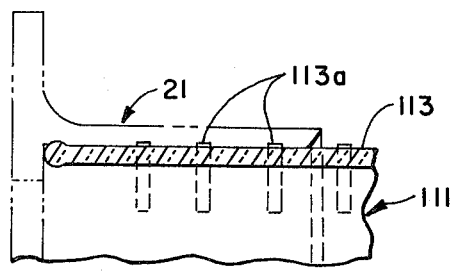
FIG. 8

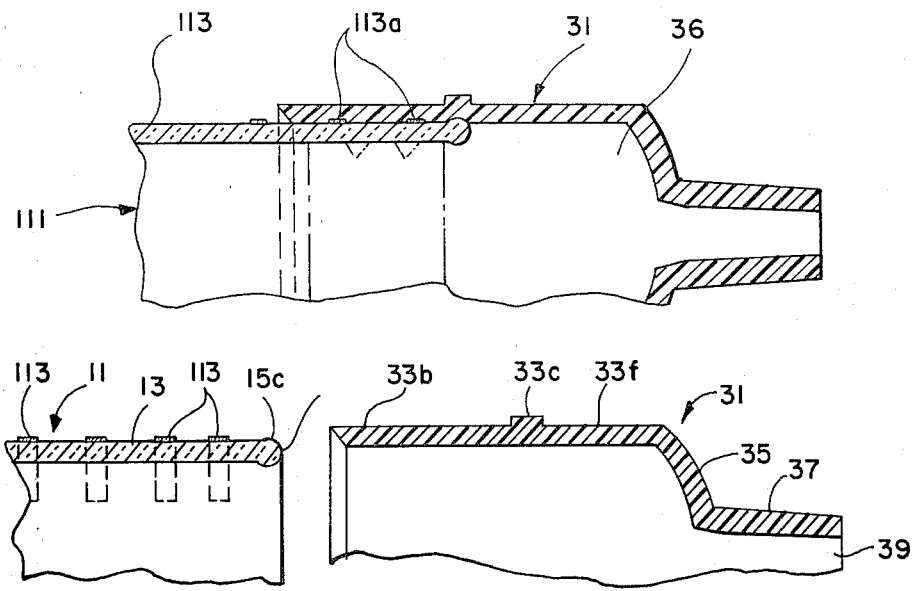
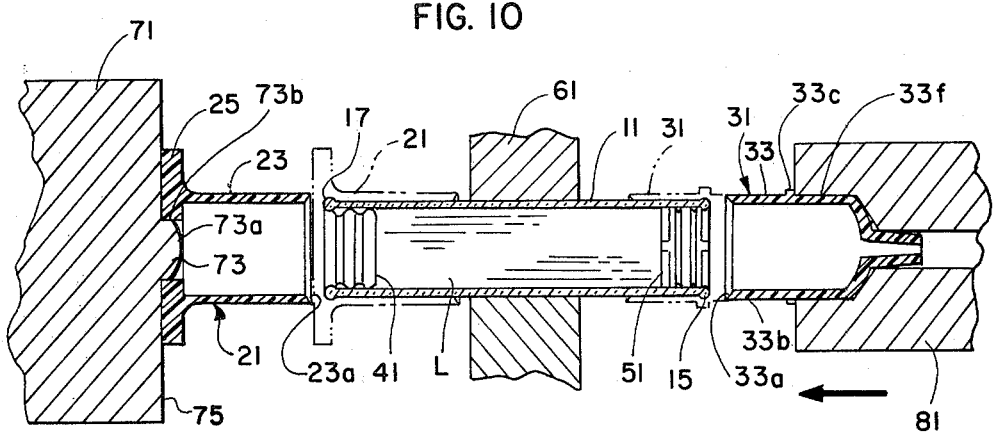

SYRINGE ASSEMBLY WITH CONTAINED POP-OUT ELASTIC PLUG SEAL

This is a division, of application Ser. No. 197,845 filed Nov. 11, 1971 now abandoned.

This invention relates to syringe assemblies for use in prefilled packaging and long-term containment and subsequent dispensing, of liquid drugs and other pharmaceutical chemicals, and to a method of assembling such.

It has been common in the syringe art to provide syringes formed from both glass and plastic materials. It is known that glass syringes have an important advantage of providing a clear and chemically inert container for drugs and other chemicals which are desired to be injected. The transparency of the glass enables the ready detection of any visible foreign particulate matter, and in addition the relatively chemically inert characteristic of syringe glass materials enables the injectable drug or chemical to be left in contact with the glass walls of the container for substantial periods of time without altering the chemical properties of the drug by combination with chemicals in the syringe material or by evaporation through the container wall of various chemical constituents in the drug or other chemical liquid. Thus, it is a particular advantage to be able to employ the advantageous properties of glass when packaging and storing drugs over a long period of time. Typically, a type of glass known as Type I or boro-silicate glass, is used for this purpose, having a high order of chemical inertness. However, this type of glass is somewhat difficult to handle in manufacturing a syringe by forming operations on a glass tube, and as a syringe formed with its entire body of glass requires the opposite ends of the glass body to be formed to provide finger-grip flanges at one end and a nose tip at the opposite end or to adhere suitable finger-grip and nose-forming glass end pieces thereto, for dispensing and attachment to further units such as hypodermic needles, or for use simply for dispensing it will be readily appreciated that such all-glass syringe bodies are troublesome and expensive to manufacture, and have other substantial drawbacks, including that of ease and danger of breakage of the end formed or secured sections, as in so forming or securing, stresses are set up in the glass, and weak spots are developed which cause the syringe to be subject to breakage at these points. This is a particularly important hazard for the finger-grip flange section, as breakage at this point may cause cutting of an operator and/or the patient. In addition, the breakage may take place in the course of handling the syringe body after formation of the flange and nose tip ends thereon, as in the course of filling the syringe, inserting a plunger piston therein, printing of the syringe body, etc. However, a special hazard is the possibility of the flange breaking during use, as all-glass syringes have been known to cause serious finger cuts due to breakage of the flange when pressure is applied during the actual injection procedure. Thus, there are two major disadvantages in the use of all-glass syringes, namely the high cost of providing the flange and nose tip end, and the hazard of breakage.

These two disadvantages of cost and breakage hazards are readily overcome by the use of plastic syringes, and particularly injection-molded plastic syringes and syringe body components; however, all-plastic syringes have been found generally unsuitable for storage of drugs and other active chemicals, and therefore are unusable for a prefilled syringe. The chemical makeup of substantially all thermoplastic and thermosetting resins is such that there is an appreciable chance of the contained drug combining with chemicals in the plastic, or in other instances the plastic may act in an absorptive fashion, having a tendency to absorb the chemicals out of the drug into the plastic, thus changing the chemical constituency and for relative proportions of the drug or other chemical liquid contained in the plastic syringe body. In addition, it is also well known that all thermoplastic resins have a moisture vapor transmission characteristic which can cause an undesired loss of fluid during long periods of storage.

In a third type of prior art syringe arrangements related to this problem, a tubular glass element has been attempted to be used with thermoplastic resin parts assembled to the glass. In such known arrangements, the thermoplastic resin parts have been secured to the glass by the use of adhesives. However, adhesive securing is slow, messy, and provides an undesirable opportunity for the adhesive material to subsequently come into contact with the contained drug or other liquid chemicals, which would of course endanger the chemical purity of the drug. In addition, while it might be possible to form a plastic member onto a glass tube through an insert mold process, such insert mold process requires very close tolerance controls, which would not normally be available when employing commercially available glass tubing, which is supplied with a fairly wide tolerance variation. Screw-on mechanical connections between a glass tube and a plastic member are generally less than wholly advantageous, as the formation of such threads on the glass tube create an expense, and in addition create stress conditions which may cause breakage, as well as require a close tolerance control to effect an effective seal in those instances where sealing may be required. While snap-over lip-type plastic cover caps have been employed in various fashions to fit over a beaded glass mouth such as a bottle mouth, such snap-over cover cap lip connection arrangements are not at all satisfactory for syringe construction, as the interference snap-fit removable interconnection formed thereby is short and interfitted for relative ease of manual removal and does not provide sufficient retentive resistance to pull-off forces to enable its satisfactory use for glass tube and plastic finger grip or nose piece connections in syringe use assemblies. Minimal reliable pull-off force resistance of the order of approximately 5–8 pounds and more is often necessary, and higher orders of resistance are desirable for insured reliability.

It is accordingly a feature of the present invention to overcome the disadvantages of the prior art described above, by providing a prefilled or prefillable syringe assembly which utilizes, according to one aspect thereof, the advantages of a glass tube as a sealed drug or other chemical storage container, while enabling the utilization of the inexpensive and reliable mechanical properties of an injectable thermoplastic resin for the finger-grip and nose-forming end sections which need not form any part of the basic liquid-containment storage chamber walls. This syringe is particularly advantageous in enabling ease of mechanical handling of the glass tube, both before and after assembly with the plastic finger grip and nose-forming end sections, during the various manufacturing operations performed thereon, including washing, feeding, sterilizing and printing of graduations or legends thereon, without the substantial disadvantages afforded in such handling and processing operations which are encountered when the tube has a glass flange formed thereon. In addition, it will be appreciated that by employment of the glass tube as the separately prefillable and sealable liquid-containment body section or cartridge unit, the open-ended glass tube may be readily utilized to contain a desired drug or other chemical liquid without necessity for the liquid to come into contact with the plastic flange during an extended storage period and may in fact be prefilled and sealed prior to assembly of the two plastic end sleeves thereon to form the finger-grip and nose therefor in the final syringe assembly. In such arrangement, the opposite ends of the glass tube may be suitably sealed off during the storage period as with a plunger piston of pharmaceutical-grade rubber or other suitable elastic material of low reactivity at the finger grip end and a further suitable pop-out, rupturable, or operable seal at the nose end. While a preferred embodiment utilizes a particular end sealed arrangement, it will be appreciated that various constructions and arrangements may be utilized within the scope and intent of the present invention.

According to a further and separately independently usable feature of the invention a syringe is provided with an improved pop-out valve seal at its nose end, which is similar to that shown in co-pending application Ser. No. 88,360 of Brian E. Baldwin, and which affords improved force transmission to the pop-out valve seal to enable it to be more easily popped out for fluid dispensing action.

In effecting my invention, various thermoplastic resins have been attempted to be employed for the finger-grip and nose-forming sleeves, and great difficulty has been encountered in attempting to resolve this problem, as the various thermoplastic resins have been found to exhibit various difficulties, including either cracking or rupturing of the finger-grip and nose-forming sleeves or breakage of the glass, insufficient retention resistance, inadequate elasticity with sufficient retention capability, too much flexibility, and long- and short-term creep, with resultant long- and short-term cracking and/or loosening. However, by careful selection of parameter limits for the glass tube and thermoplastic finger grip, I have been able to successfully form a glass tube and thermoplastic resin finger grip assembly which may be simply and reliably manufactured and utilized. A particular thermoplastic resin material which I have found usable in practicing this aspect of my invention is polypropylene.

The present invention is therefore directed to a glass tube and thermoplastic resin finger grip sleeve assembly and method of assembly thereof, the details of which are described in the course of the following description of the invention.

Still other objects, features and attendant advantages will become apparent to those skilled in the art from a reading of the following detailed description, taken in conjunction with the accompanying drawings wherein:

FIG. 5 is a longitudinal section view of the finger-grip sleeve and the adjacent open end of the glass tube of FIG. 1, prior to assembly.

FIG. 6 is a perspective view of the pop-out valve seal plug of FIG. 1.

FIG. 7 is a fragmentary longitudinal section view of a modified tube and finger grip assembly.

FIGS. 8 and 9 are longitudinal fragmentary section view of further modifications according to the invention.

FIG. 10 is a longitudinal section view of the nose-forming sleeve and adjoining end of the glass tube prior to assembly.

FIG. 11 illustrates a method of assembly according to the invention, of the syringe arrangement of FIG. 1.

Figure 1:
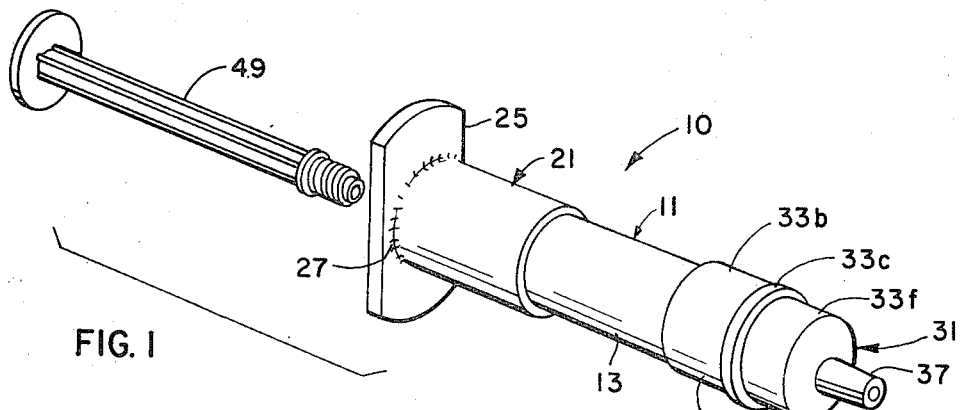
FIG. 1 is a perspective view of a preferred prefilled syringe embodiment constructed in accordance with the invention.
Figure 2:
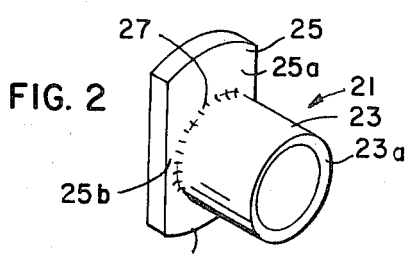
FIGS. 2 and 3 are perspective views of the finger-grip sleeve and nose-forming sleeve of the embodiment of FIG. 1.
Figure 3:
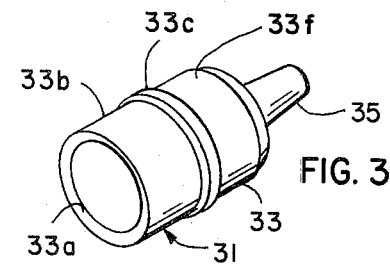

Referring now in detail to the figures of the drawing, a prefilled or prefillable syringe body assembly 10 includes a liquid-containment chamber formed by a straight cylindrical glass tube 11 and two opposite end seals 41 and 51. The syringe body also includes a finger-grip sleeve 21 and a nose-forming sleeve 31 formed of thermoplastic resin, namely polypropylene, and secured along the opposite ends of the glass tube 11 through a long wall-engaging interference fit. Seal 41 is an elastic plunger piston of pharmaceutical-grade rubber or other suitable material of low chemical reactivity, and to which a manual plunger 49 may be removably secured, and seal 51 takes the form, in the preferred embodiment, of a pop-out valve seal plug of pharmaceutical-grade rubber or other suitable elastic material of low chemical reactivity. The glass tube may suitably be formed of a length of straight cylindrical tubing which may be conventionally formed by a die-formed melt process, and subsequent cutting into sections to form desired lengths of glass tubing to be utilized for the glass tube 11. Glass tube 11 includes a straight cylindrical tubular wall 13, which is preferably fire-polished at its opposite ends 15 and 17 to form a fire-polished bead thereon. As an alternative, the opposite ends may be lightly or heavily beveled at their outer annular edge as by grinding or sanding. The fire-polished beads 15a and 17a, at the respective tube ends 15 and 17, may be conventionally formed, and preferably are relatively small, adding on the order of 0.001–0.005 inch diameter to the external diameter of the glass tube, although greater bead size formations may be utilized for given end uses, particularly where internal diameter restrictions are not critical or of material importance. Likewise, while the fire-polished bead 17a is of some material advantage in enhancing the retentive capability of the finger grip 21 on the glass tube 11, fire-polishing without formation of a noticeable bead may be effected, as by employing a forming mandrel, to an acceptable extent of end sleeve assembly capability.

The finger grip sleeve 21 is formed with a finger grip section 25 and a tubular sheath 23 which frictionally engages with the outer longitudinal surface of the glass tube 11 adjoining end 17, and nose-forming sleeve 31 has a dispensing/connecting tip integrally connected through an end wall 35 to a tubular sheath section 33, which frictionally engages in an interference fit with the adjoining longitudinal outer surface of the glass tube 11 adjoining end 15 thereof. Both sleeves are frictionally cam-stretched into interference fit over and along the respective contiguous longitudinal end wall surfaces of glass tube 11, and as the applicable parameter considerations for both sheaths 23 and 33 relative to glass tube 11 are generally the same, the parameter considerations will first be discussed with respect to the finger grip sleeve 21, and various differences applicable to nose-forming sleeve 31 will then be discussed. As is seen in FIG. 5, the tubular sheath section 23 of the finger grip sleeve 21 has an inner wall surface 23c which has a lesser radius than the outer radius of tubular wall 13 of glass tube 11, by an interference amount indicated by the reference character A, the increase in radius of the glass tube by the head 17a being indicated by the reference character B. Thus, the increase in diameter afforded by the head 17a is 2B, and the diameter interference between the exterior diameter of the tube wall 13 and the tubular sheath inner wall surface 23c is 2A, according to the reference characters of this Figure. This interference value 2A is of substantial criticality in affording successful operation in accordance with the invention, particularly in light of the conventional practice of supplying glass tubing with a fairly wide tolerance range of diameters from a nominal specified diameter, as practical utilization of the invention requires that the tubing either be utilized as directly supplied from the manufacturer or by internal sorting at some point prior to assembly use, to reduce the tolerance limits to an acceptable range. It has been found that the present invention may be practiced within the tolerance limits of glass tubing as such is conventionally supplied, according to one preferred inventive aspect and mode of practice, and according to a broader but substantially less desirable aspect and mode of practice by sorting the glass tubing and reducing the tolerance levels between the glass tubes of a given lot to an acceptable level for utilization according to this less desirable modified form of practicing the invention. Thus, the preferred embodiment of the invention in which the thermoplastic resin is preheated and is in a heated state during assembly, as will be later described may be practiced as applied to standard die-form glass tubing and thermoplastic resin in the form of polypropylene with glass tube tolerance levels of the order of approximately 0.034–0.035 inch diameter variations of standard commercially supplied glass tubing of approximately 0.4 inch outer diameter, as supplied in readily available commercial lots, and the modified and less desirable aspect of the invention may be practiced with the aid of sorting with tolerance levels for this diameter of glass tubing reduced to approximately 0.025–0.027 inch.

In addition, the head 17a may be, for a given tolerance range, of greater consequence in the modified form, and may be preferably held to a minimum, as of the order of 0.001–0.002 inch raised diameter increase for this and other practical considerations of use.

One or both of the end 17 of tube 11 and the facing end 23a of sheath 23 is formed with a cam surface which exerts a radially and circumferentially stretching action on the sheath 23 as a function of pressing of the sheath 23 axially against and onto the open end 17 of glass tube 11. As the glass tube 11 itself is essentially rigid as compared to the polypropylene sleeve 21, the caming action will result in the tube sheath 23 stretching in diameter and circumference and forming an elastically enlarged contiguous binding ring of substantial longitudinal extend about and along the longitudinal annular surface of tube 11 upon the complete pressing of the tubular sheath 23 of finger grip sleeve 21 onto the glass tube 11. This also sets up internal stresses in both the sleeve sheath 23 and the glass tube 11, which must be accommodated in practicing the invention.

Figure 4:
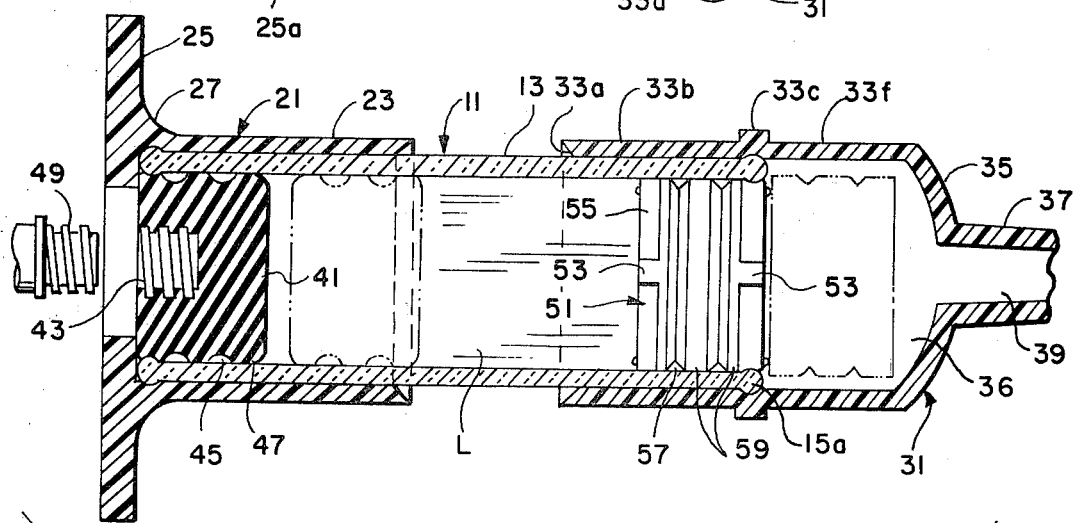
FIG. 4 is a longitudinal section view of the embodiment of FIG. 1.

This interference stretch-fit press-on of the finger grip sleeve 21 is preferably terminated by an annular shoulder 29 forming a radially inward extension of the rear finger grip flange section of the finger grip sleeve 21. A preferred form of the shoulder 29 is shown in FIGS. 4 and 5, in which the shoulder 29 extends radially inwardly to form a thru-bore 28 which is of lesser diameter than the effective internal diameter of the glass tube 11, thereby affording a shoulder stop which will prevent or render difficult the removal of a plunger piston after insertion, as by insertion through the opposite end of the tube 11, and will enable the thru-bore 28 to be utilized for removable connection and operation of manually operable plunger 49 to be connected and/or removed therethrough. Another form of a shoulder 129 is illustrated in FIG. 7 at 129, in which the shoulder 129 forms a thru-bore 128 which is of at least as great a diameter as the effective internal diameter of the tube 11. This is normally less desirable in the loss of the piston stop function of shoulder 19, however this construction does enable the ready insertion and removal through the thru-bore 128 of a conventional or other elastic plunger piston 41, though the thru-bore 128, if such should be desired for assembly and/or disassembly of the syringe 10, while also enabling plunger 49 to be operated therethrough by external manual manipulation.

Finger grip section 25 is formed in the illustrative and preferred embodiment as an integral flange having an enveloping annular portion including opposed extensions 25a and connecting side portions 25b. Other finger grip forms and constructions may be employed, including an annular flange having a constant diameter providing a round flange periphery, or the finger grip section may have integral molded finger-gripping rings, or other suitable finger grip element or elements. However, the illustrative embodiment is preferred, and particularly in employing a fully annular enveloping flange portion extending laterally beyond the outer diameter of the sheath 23 and enabling the employing of annular fillet enlargement 27, particularly in the embodiments employing a fire-polished bead 17a on the end of the glass tube 11.

As previously stated, one or both of the end 17 of tube 11 and end 23a of sheath 23 is formed with a cam surface which effects a circumferential and diameter-stretching action on the sheath 23 as a function of pressing of the sheath 23 axially against and onto the open end of glass tube 11. A cam surface on the end of finger grip sleeve sheath 23 may be formed as an annular bevel cam surface 23a, as shown, which may have an annular blunting beveled or flat surface formed at its radially outer edge, if desired, or which may be omitted if outer edge blunting is not desired. Alternatively, the surface 23a may be rounded or otherwise arcuately smoothly curved as viewed in longitudinal section, to provide the desired camming surface action with the end 17 of glass tube 11. Glass tube end 17 is preferably fire-polished to form a smooth radially outer end edge surface 17aa, which preferably forms a small bead of approximately 0.001–0.005 inch added diameter, and which bead will normally extend beyond the nominal cylindrical diameter of the tube 11 both radially outwardly and radially inwardly, as well as providing the desired convex arcuate outer cam surface 17aa for camming interengagement with the interfacing end edge of sheath 23. (In this respect it will be appreciated that the drawings are largely schematic and that various parts or elements, such as bead 17a, have been exaggerated for purposes of illustration and clarity.) This small annular fire-polished bead serves a desired multiple purpose of cam-stretching of the sheath as it is press-fit in enveloping interference fit over the end 17 and onto the longitudinal straight wall surface 13 of the tube 11, as well as providing added retentive gripping effect and added strength to the glass tube at the end 17. The glass tube end 17 may alternatively be ground or otherwise formed with a beveled or rounded outer end edge surface corresponding to surface 17aa, which may enable effecting of the desired cam action stretch-fitting on the sheath 23. Also alternatively, the sheath 23 may have its initially interfacing end edge blunt, without the highly desired dual camming provided by both bevel 23a and bead 17a, although it will be appreciated that a sharp outer annular edge surface on the tube 11 is not desirable in any event as such will ordinarily effect a scraping and material-removal action in attempting to insert the tube into the sheath 23, with consequent difficulty in assembly and reduction is retentive resistance of the sheath on the tube.

The fillet 27 forms an integral smoothly connecting annular corner between annular sheath 23 and annular finger grip flange section 25. Fillet 27 serves also as an effectively elastic smoothly enlarged diameter reinforcement for the sheath 23 at the zone where the sheath 23 overlies the bead end 17a of tube 11. This smooth enlargement provided by the fillet 27 provides added strength and desirable lateral stress distribution in this zone, while enabling the sheath to adequately stretch in diameter and compress in thickness, without the cracking of glass tube 11 that might be caused by bottoming or terminating the glass tube end 17 in a zone within the grossly circumferentially enlarged and more rigid zone within the annular finger grip flange section 25, as well as enabling the material of the sleeve in the zone of fillet 27 to compensate for the added thickness of diameter of bead 17a and the expansion of sheath 23 necessary for the accommodation of the basic interference fit formed between the straight-walled section 13 of tube 11 with sheath 23 in this end overlie and flange grip connecting inner connection transition zone 27.

The invention has been applied in practical form to available glass tubing and employing polypropylene thermoplastic resin sold by Rexall, the utilized polypropylene resin being a heat-stabilized grade marketed as Retail PP-13S, 12 melt index. Glass tubing of a nominal cylindrical outer diameter along the cylindrical wall 13 of 0.414 inch, with a conventionally supplied tolerance range in diameter of approximately 0.034 inch, has been suitably utilized accordng to the preferred aspect of the invention. In this respect the thickness of sheath 23 may be suitably of the order of approximately 0.020–0.040 inch, and preferably in the range of 0.030–0.035 inch, the length of the sleeve sheath 23 being within the range of approximately 0.4–0.7 inch in order to afford an adequate longitudinal extent of contiguous interfacing longitudinal wall seated interference retention fit between the sheath 23 and tube 11. The cylindrical inner wall 23c of sheath 23 may be very slightly tapered inwardly therealong from its open end adjacent annular beveled edge 23a, to the zone adjacent shoulder 29, as of the order of approximately 0.002 inch diameter change. The fillet enlargement may have a radius of approximately 0.025–0.250 inch and preferably is in the range of approximately 0.100 inch for these sizes of sleeves and tubes. Glass tubes of the order of 0.020–0.040 inch or greater wall thickness may suitably be employed, using available commercial grades of glass, although tubing wall thickness of the order of as low as 0.010–0.015 inch may be utilized when employing high-strength glass for the glass tube 11. However, the smaller wall thicknesses are normally difficult to form and handle in other respects, and will not normally be desirable or necessary.

The indicated tolerance range which is available on a commercial basis from manufacturers of die-formed glass tubing in the illustrative example of approximately 0.4 inch nominal outer diameter, namely approximately 0.034 inch tolerance, may be satisfactorily accommodated according to the invention by practicing the preferred mode of assembly of the tube 11 and sleeve 21 although the lower end of the tolerance range will not give as good pull-off resistance as the more desirable mid and upper portions of the tolerance range for a given sleeve size adapted to cover the total range of these tolerance variations, and sorting may be resorted to, if desired, to effectively increase the lower values of retentive resistance. In this preferred mode of assembly, the sleeve 21, which may be conventionally injection-molded, is first preheated prior to assembly to an elevated temperature and substantially above normal ambient room temperature, and the sleeve 21 is assembled with the glass tube 11 while the sleeve 21 is at such elevated temperature. It has been found suitable to heat the sleeves 21 to an elevated temperature of the order of approximately 100°–160°F, although it is believed that temperatures within a range of values slightly below and substantially above this temperature range may suitably be employed, dependent to an extent upon the tolerance limits which must be accommodated in glass tubing sizes, it being appreciated that the upper temperature should not reach the tacky temperature zone for the thermoplastic resin forming the sleeve 21. It has been found that by employing this preheating of the sleeve 21 and assembly of such with the glass tube 11 while in an elevated temperature condition, the range of interference tolerance which may be operably acceptable, between the internal diameter of the sheath 23 and its inner surface 23c and the normal outer wall diameter along the straight cylindrical wall section 13 of tube 11, may be substantially extended to accommodate commercial tolerance ranges of glass tubing, without requiring sorting. Thus, as noted, tolerance ranges of the order of approximately 0.034 inch for the outer diameter of glass tubing 11 of approximately 0.4 inch nominal outer diameter may be accepted and used direct, without requiring sorting, while still providing adequate crack resistance of the polypropylene thermoplastic resin sleeve 21, and without causing cracking of the glass tubing 11, either during, immediately after, or after long-term storage of, the assembly 11, 21.

As noted heretofore, the nose-forming sleeve 31 is assembled onto glass tube 11 in the same manner and with essentially the same parameter criteria of entrance configurations, relative wall diameters, thicknesses, and longitudinal lengths of annular inter-wall engagement. In addition, in the illustrative embodiment, the sheath section 33 of nose-forming sleeve 31 has an extension section 33f which extends beyond the end 15 of glass tube 11, and may be form a cavity 36 which is bounded on each end by tube end 15 and sleeve end wall 35. In this embodiment the sleeve 31 also has an annular sheath mid-section enlargement in the form or raised ring 33c which may serve a dual function of aiding in longitudinal positioning and force-transmitting press-on of the sleeve 31 by a female work holder and of providing an annular reinforcement which is desirably positioned over or closely adjacent the zone of end 15 of glass tube 11. For a polypropylene nose-forming sleeve 31 having an outer diameter of approximately 0.46 inch and an inner wall diameter of approximately 0.4 inch, with a forwardly decreasing diameter taper of approximately 0.001–0.004 inch along a total internal sheath wall length of approximately 0.76 inch, a ring enlargement of approximately 0.05 inch longitudinal width and approximately 0.51 inch outer diameter, with sheath extent 33b having a length of approximately 0.46 inch, has been found satisfactory for glass tubing of approximately 0.4 inch outer diameter, as previously discussed in relation to finger grip sleeve 21. Connector/dispenser tip 37 has a fluid discharge bore 39 formed therein, and may if desired be formed for suitable connection thereof to a needle unit, as by forming a Luer taper on tip 37, or a threaded connector surface, or other connection may be formed on sleeve 31 if and as may be desired. Also, while the illustrated nose-forming sleeve 31 is the much preferred and superior embodiment enabling various syringe combination constructions to be employed, including various tube seal arrangements, it will be appreciated that modifications may be made, as for instance the sheath extension 33f may be omitted and the end wall 35 may be bottomed against or brought closely adjacent tube end 15.

In the illustrated and preferred embodiment, valve seal plug 51 forms an elastic pop-out by-pass valve seal element which is initially self-retained in elastic sealing relation within glass tube end 15. Sleeve sheath section 33f and end wall 35 form, together with the end surface of tube end 17, an enlarged cavity which is larger in effective circumference than the effective sealing length of plug seal by-pass valve element 51. In addition, valve 51 has fluid bypass depressions 55 and raised surfaces 53 on its forward and rearward faces to insure fluid flow around plug 51, independent of whether the plug be partially retained in the end of tube 11 and/or in forward engagement with the end wall 35 of cavity 36. The raised surfaces 53 preferably take a cruciform configuration, as illustrated. By employing this bypass seal plug 51 in the present syringe form with the straight-walled substantially constant diameter glass tube body section 11, improved force transmission is effected from piston 41 through liquid L to bypass plug seal 51, in view of the plug seal 51 having a maximum rear surface onto which pop-out pressure may be exerted through liquid L. Thus less pressure may be required to be exerted on plunger 49 for pop-out of bypass valve plug seal 51 than would be required with a bypass valve plug seal fitted within a reduced neck tube section, as illustrated in the copending application Ser. No. 88,360, mentioned supra.

The invention may also be practiced by assembling the sleeves 21 and 31 onto the glass tube 11 while both the sleeves and the glass tube are at the normal ambient room temperatures; however, the maximum acceptable interference fit in this less desired mode of practice of the invention, as applied to standard glass tubing and polypropylene thermoplastic resin sleeves 21, 31 has been found to be approximately 0.030 inch, and the range of tolerances which may be accommodated in the outer diameter of the glass tubing is substantially reduced, and will be of the order of approximately 0.025–0.027 inch, as the lower limit acceptable interference fit is approximately 0.003–0.005 inch, as distinguished from the substantially wider interference fit tolerance range extending from a lower limit of approximately 0.003–0.005 inch to an upper limit of approximately 0.037–0.039 inch which has been found to be operable for the preferred heated sleeve mode of assembly as discussed above. In addition, in the less desired mode of practice in which sleeves 21 and 31 are assembled cold, substantial residual stresses do remain in the sleeve 21 to an extent that such may, particularly after a long-term storage, result in the cracking of the end sleeves along their respective sheaths 23, 33, where the outer extent of the interference tolerance zone of approximately 0.030 inch is required or approached for a particular sorting utilization of glass tubing.

In a particular illustrative embodiment which utilizes glass tubing of nominal 0.414 inch outer diameter along the surface of the straight cylindrical wall section 13, and which was supplied within a specified commercial tolerance range of 0.401–0.435 inch, a polypropylene thermoplastic resin finger grip sleeve 21 has been employed with a sheath inner diameter of approximately 0.398 inch at its entrance end and approximately 0.396 inch adjacent shoulder 29, and a nose-forming sleeve 31 has been employed having a sheath inner diameter of approximately 0.398 inch at its entrance end and approximately 0.396 inch adjacent end wall 35, utilizing the preferred preheated sleeve assembly method, it being noted that the resulting range of tolerances lies within the acceptable range of interference fit. The same nominal glass tube diameter of 0.414 inch may also be used in the less desired cold assembly method, with approximately the same inner wall 23c diameter for the sheaths 23 and 33, by reducing the tolerance range of the glass tubing to within the acceptable tolerance of approximately 0.025–0.027 inch. In this illustrative embodiment, the sheath 23 has a total length of approximately 0.6 inch, and the fillet 27 has a radius of curvature of approximately 0.100 inch, with the finger grip flange section 25 having a longitudinal thickness of approximately 0.9 inch. In further note of the cavity-forming zone 33f beyond the end 15 of tube 11, it has been found that there is a stress-related step-down of outer and inner sheath diameters directly beyond the tube and 15, the remaining extended extent of sheath 33 beyond end 15 being of approximately original molded or otherwise pre-assembly size, less any small extent of residual shrinkage effected by the heating operation during assembly.

Glass tube and polypropylene thermoplastic resin sleeve syringe assemblies 10 constructed in accordance with the foregoing description have been found to provide sleeve pull-off resistance within the range of approximately 5 to 35 pounds, when the glass tube 11 is in a clean condition without lubricant such as silicone thereon. When the glass tube 11 has silicone coating thereon, as may sometimes be desirable for other operational conditions such as the subsequent insertion of a plunger piston or slidable plug in the glass tube, the retentive resistance formed by the interference fit between the sleeves 21 and 31 and the glass tube 11 has been found to be reduced by the order of approximately 20 percent, and accordingly the lower range of interference tolerances may not be acceptable for a given required use where the retention force required for utilization of the assembly in a given instance may be greater than the retentive resistance afforded by this lower range of tolerance fit. Such deficiency may be overcome by sorting, or otherwise insuring that the interference fit is sufficient to provide the desired retentive resistance to pull-off of the sleeves 21 and 31 from the glass tube 11.

A modified form of practice of the invention is illustrated to FIGS. 8 and 9, in which the glass tube 111 has raised spaced protrusions 113a on its surface, as may be provided by printing of graduations, legends, etc. on the glass tube prior to assembly with the sleeve 21. This printing may be formed as by application of epoxy ink which is subsequently cured in situ on the glass tube or by the application of ceramic ink subsequently fired in place on the glass tube, the utilization of such inks to form graduations and other indicia being commonly and readily understood in the art, and such will accordingly not be further described herein, other than to note that such may suitably provide a raised added wall thickness and enlargement of the order of approximately 0.001–0.002 inch. As will be noted from FIGS. 8 and 9, these raised surface segments 113a lie beneath one or both of the sheaths 23 and 25 end sleeves 21 and 31, and afford additional retentive resistance to the removal of the finger grip flange in the course of usage of the syringe 10. While depressions may also be formed in the glass tube outer wall surface, for added retentive resistance, untempered scoring to form such depressions is not desirable as the glass is subsequently weakened along such score lines, which may result in subsequent cracking during or after assembly.

In practicing the invention, the liquid L to be prefilled and packaged in syringe 10, is preferably prefilled in glass tube 11 and sealed by piston seal 41 and valve seal 51 prior to assembly of plastic end sleeves 21 and 31 thereon. Preferred simultaneous assembly of the finger grip sleeve 21 and nose-forming sleeve 21 onto the prefilled and sealed body cartridge unit formed by glass tube 11 and plunger piston seal 41 and pop-out valve seal plug 51, may then be effected, and is illustrated in FIG. 11, in which a work holder 71 having a gripping nipple 73 with a tapered nose 73a and cylindrical gripping surface 73b engages in releasable frictional holding relation with the bore-forming surface of shoulder 29 on a sleeve 21 and in which glass tube 11 is held in a suitable guide chuck 61 which may be suitably formed by a V-chuck, with the glass tube either vertical or horizontal and further utilizing a female work holder 81 for nose-forming sleeve 31 to be fitted onto the opposite tube end 15. The work holders 71 and 81 are moved toward the glass tube 11 to move the respective opposite ends of sleeve sheaths 23 and 33 into end contact with an into cam stretch-fitted interference gripping relationship about a relatively long extent of each respective end of the glass tube 11, the force required for this being transmitted through the forward face 75 of work holder 71 and the forward face and internal holding cavity of work holder 81. After completion of assembly, the assembly 11, 21, 31 may be released from the chuck 61, and the entire procedure may be repeated with a succeeding glass tube and finger grip sleeve.

In operation, the operator assembles conventional screw-in plunger 49 into plunger piston 41, and presses the plunger 49 and piston forward, thus transmitting forward pressure and force through liquid L onto pop-out plug seal 51 to thereby effect movement of the bypass valve plug seal 51 into chamber or cavity 36, and enable the bypass passage of liquid L into cavity 36 and about and past bypass valve plug seal 51 and out through discharge bore or orifice 39 in nose tip 37.

While the invention has been illustrated and described with respect to various preferred and other embodiments and modes of practice thereof, it will be appreciated that various modifications may be made without departing from the scope and spirit of the invention. Accordingly, the invention is not to be limited by the illustrative embodiment but only by the scope of the appended claims.

I claim:

1. A glass tube and non-glass finger grip and nose-forming arrangement for use particularly in packaging and subsequent dispensing of chemicals, comprising
   a substantially cylindrical glass tube formed of a length of substantially constant diameter thin-walled glass tubing of substantially constant wall thickness along its length and having a wall thickness substantially smaller than the outer and inner wall diameters of said glass tubing,
   a finger-grip sleeve of thermoplastic resin and having a tube-gripping sheath section laterally extending finger-grip protrusion integrally formed thereon,
   and a nose-forming sleeve of thermoplastic resin and having a reduced diameter section integral with a tube-gripping sheath section thereof,
   said sleeves being frictionally secured in annularly extending stretch-fit along their sheath sections over and along respectively opposite ends of said glass tube,
   a piston slidably disposed in sealing relation within and at said end of said glass tube having said finger-grip sleeve thereon,
   a valve seal disposed at the opposite nose end of said glass tube,
   said reduced diameter section of said nose-forming sheath including a laterally extending wall spaced longitudinally forwardly of the respective adjacent end of said glass tube and having a reduced diameter central orifice formed therein for fluid flow therethrough during dispensing,
   said nose-forming thermoplastic resin sleeve sheath section extending longitudinally beyond the respective overlain said end of said glass tube to form a fluid flow by-pass cavity of larger internal diameter than the internal diameter of said cylindrical glass tube,
   and said valve seal being a pop-out elastic plug frictionally sealing the nose sleeve end of said tube,
   said plug having a free relaxed diameter and length size less than the corresponding diameter and length sizes of said fluid flow by-pass cavity at all corresponding annular and longitudinal points along the length and annular periphery of said plug and said by-pass cavity to enable free plug movement within said by-pass cavity and fluid by-pass flow around the annular periphery of said pop-out valve plug when such plug is longitudinally popped out into said by-pass cavity by forward motion of said plunger.

2. A glass tube and non-glass finger grip and nose-forming arrangement for use particularly in packaging and subsequent dispensing of chemicals, comprising
   a substantially cylindrical glass tube, a finger-grip sleeve of thermoplastic resin and having a tube-gripping sheath section laterally extending finger-grip protrusion integrally formed thereon, and a nose-forming sleeve of thermoplastic resin and having a reduced diameter section integral with a tube-gripping sheath section thereof, said sleeves being stretch-fit along their sheath sections over and onto respectively opposite ends of said glass tube, a piston slidably disposed in sealing relation within and at said end of said glass tube having said finger-grip sleeve thereon, a valve seal disposed at the opposite nose end of said glass tube, and a dispensable liquid contained within said tube between said piston and said valve seal, said reduced diameter section of said nose-forming sheath including a laterally extending wall spaced longitudinally forwardly of the respective adjacent end of said glass tube and having a reduced diameter central orifice formed therein for fluid flow therethrough during dispensing, said nose-forming thermoplastic resin sleeve sheath section extending longitudinally beyond the respective overlain said end of said glass tube to form a fluid flow cavity of larger internal diameter than the internal diameter of said cylindrical glass tube, and said valve seal being a pop-out elastic plug frictionally sealing the nose sleeve end of said tube, said plug having a free relaxed diameter and length size less than the corresponding diameter and length sizes of said fluid flow cavity and having a channeled forward face to ensure fluid flow therearound and through said reduced diameter orifice upon popping said valve plug into said cavity by forward motion of said piston and contained liquid, said valve seal elastic plug having a cruciform forward and rear face forming fluid flow channels on each of said forward and rear faces.

3. A glass tube and non-glass finger grip and nose-forming arrangement for use particularly in packaging and subsequent dispensing of chemicals, comprising a substantially cylindrical glass tube having fire-polished slightly enlarged opposite ends, a finger-grip sleeve of thermoplastic resin and having a tube-gripping sheath section laterally extending finger-grip protrusion integrally formed thereon, and a nose-forming sleeve of thermoplastic resin and having a reduced diameter section integral with a tube-gripping sheath section thereof, said sleeves being stretch-fit along their sheath sections over and onto respectively opposite ends of said glass tube, a piston slidably disposed in sealing relation within and at said end of said glass tube having said finger-grip sleeve thereon, a valve seal disposed at the opposite nose end of said glass tube, and a dispensable liquid contained within said tube between said piston and said valve seal, both of said sleeve sheaths having a laterally outwardly extending annular enlargement section at and in substantial lateral encompassing relation with the respective annular fire-polished end bead on said glass tube, said finger-grip sheath annular enlargement being a fillet connecting with an annular finger-grip section, said annular enlargement on said nose-forming sleeve forming a raised ring disposed in spaced relation from the opposite longitudinal ends of its respective said sheath section.

4. A glass tube and non-glass finger grip and nose-forming arrangement for use particularly in packaging and subsequent dispensing of chemicals, comprising a substantially cylindrical glass tube having fire-polished slightly enlarged opposite ends, a finger-grip sleeve of thermoplastic resin and having a tube-gripping sheath section laterally extending finger-grip protrusion integrally formed thereon, and a nose-forming sleeve of thermoplastic resin and having a reduced diameter section integral with a tube-gripping sheath section thereof, said sleeves being stretch-fit along their sheath sections over and onto respectively opposite ends of said glass tube, a piston slidably disposed in sealing relation within and at said end of glass tube having said finger-grip sleeve thereon, a valve seal disposed at the opposite nose end of said glass tube, and a dispensable liquid contained within said tube between said piston and said valve seal, said reduced diameter section of said nose-forming sheath including a laterally extending wall spaced longitudinally forwardly of the respective adjacent end of said glass tube and having a reduced diameter central orifice formed therein for fluid flow therethrough during dispensing, said nose-forming thermoplastic resin sleeve sheath section extending longitudinally beyond the respective overlain said end of said glass tube to form a fluid flow cavity of larger internal diameter than the internal diameter of said cylindrical glass tube, and said valve seal being a pop-out elastic plug frictionally sealing the nose sleeve end of said tube, said plug having a free relaxed diameter and length size less than the corresponding diameter and length sizes of said fluid flow cavity and having a channeled forward face to ensure fluid flow therearound and through said reduced diameter orifice upon popping said valve plug into said cavity by forward motion of said piston and contained liquid, both of said sleeve sheaths having a laterally outwardly extending annular enlargement section at and in substantial lateral encompassing relation with the respective annular fire-polished end bead on said glass tube.

5. An arrangement according to claim 4, said finger-grip sheath annular enlargement being a fillet connecting with an annular finger-grip section.

6. A glass tube and non-glass finger grip and nose-forming arrangement for use particularly in packaging and subsequent dispensing of chemicals, comprising a substantially cylindrical glass tube having fire-polished beaded opposite ends, a finger-grip sleeve of thermoplastic resin and having a tube-gripping sheath section laterally extending finger-grip protrusion integrally formed thereon, and a nose-forming sleeve of thermoplastic resin and having a reduced diameter section integral with a tube-gripping sheath section thereof, said sleeves being stretch-fit along their sheath sections over and onto respectively opposite fire-polished beaded ends of said glass tube, a piston slidably disposed in sealing relation within and at said end of said glass tube having said finger-grip sleeve thereon, a valve seal disposed at the opposite nose end of said glass tube, and a dispensable liquid contained within said tube between said piston and said valve seal, said reduced diameter section of said nose-forming sheath including a laterally extending wall spaced longitudinally forwardly of the respective adjacent end of said glass tube and having a reduced diameter central orifice formed therein for fluid flow therethrough during dispensing, said nose-forming thermoplastic resin sleeve sheath section extending longitudinally beyond the respective overlain said end of said glass tube to form a fluid flow cavity of larger internal diameter than the internal diameter of said cylindrical glass tube, and said valve seal being a pop-out elastic plug frictionally sealing the nose sleeve end of said tube, said plug having a free relaxed diameter and length size less than the corresponding diameter and length sizes of said fluid flow cavity and having a channeled forward face to ensure fluid flow therearound and through said reduced diameter orifice upon popping said valve plug into said cavity by forward motion of said piston and contained liquid, and an annular enlargement on said nose-forming sleeve forming a raised ring disposed in spaced relation from the opposite longitudinal ends of its respective said sheath section and in substantial lateral encompassing relation about the respective said fire-polished end bead.

7. A glass tube and non-glass finger grip and nose-forming arrangement for use particularly in packaging and subsequent dispensing of chemicals, comprising
a substantially cylindrical glass tube,
a finger-grip sleeve of thermoplastic resin and having a tube-gripping sheath section laterally extending finger-grip protrusion integrally formed thereon,
and a nose-forming sleeve of thermoplastic resin and having a reduced diameter section integral with a tube-gripping sheath section thereof,
said sleeves being stretch-fit along their sheath sections over and onto respectively opposite ends of said glass tube,
a piston slidably disposed in sealing relation within and at said end of said glass tube having said finger-grip sleeve thereon,
a valve seal disposed at the opposite nose end of said glass tube,
and a dispensable liquid contained within said tube between said piston and said valve seal,
said reduced diameter section of said nose-forming sheath including a laterally extending wall spaced longitudinally forwardly of the respective adjacent end of said glass tube and having a reduced diameter central orifice formed therein for fluid flow therethrough during dispensing,
said nose-forming thermoplastic resin sleeve sheath section extending longitudinally beyond the respective overlain said end of said glass tube to form a fluid flow cavity of larger internal diameter than the internal diameter of said cylindrical glass tube,
and said valve seal being a pop-out elastic plug frictionally sealing the nose sleeve end of said tube,
said plug having a free relaxed diameter and length size less than the corresponding diameter and length sizes of said fluid flow cavity and having a channeled forward face to ensure fluid flow therearound and through said reduced diameter orifice upon popping said valve plug into said cavity by forward motion of said piston and contained liquid,
said pop-out valve plug having a raised cruciform forward surface.

8. An arrangement according to claim 7, said pop-out valve plug having raised cruciform forward and rearward surfaces.

9. An arrangement according to claim 8, said pop-out valve plug having a plurality of annular sealing rings and grooves formed on its annular surface.

10. An arrangement according to claim 9,
a sloped annular cam surface formed on one of the longitudinally inner end of said sheath section of said finger-grip sleeve and the respective longitudinally outer said end of said glass tube,
and a sloped annular cam surface formed on one of the longitudinally inner end of said sheath section of said nose-forming sleeve and the respective said end of said glass tube.

11. An arrangement according to claim 10, at least one of said sloped annular cam surfaces being formed on said one end of said glass tube.

12. An arrangement according to claim 11, at least one of said sloped annular cam surfaces being an annular bevel.

13. An arrangement according to claim 11, at least one of said sloped annular cam surfaces being smoothly arcuate in longitudinal section.

14. An arrangement according to claim 13, at least one of said sloped annular cam surfaces being formed by and as a part of an annular fire-polished rim formed on one end of said glass tube.

15. An arrangement according to claim 14, said annular fire-polished rim comprising a fire-polished raised annular bead, and said fire-polished bead being formed at both longitudinal ends of said glass tube.

16. An arrangement according to claim 10, said sloped annular cam surfaces being formed on the respective longitudinally inner end each of said sleeve sheaths and facing away from the respective overlain longitudinal ends of said glass tube in the mutually assembled position of said tube and sleeves.

17. An arrangement according to claim 16, said sloped annular cam surface being formed on both longitudinal ends of said tube and on said longitudinally inner ends of both of said sleeves.

18. An arrangement according to claim 17, at least one end of said glass tube having an annular fire-polished rim smoothly arcuate in longitudinal section, formed thereon and forming said annular cam surface,
said annular fire-polished rim comprising a fire-polished raised annular bead.

19. An arrangement according to claim 18, said finger-grip sleeve having at its axially outer end an internal shoulder stop adjacent and extending into the longitudinally extended path of said glass tube one end.

20. An arrangement according to claim 19, said shoulder stop extending radially inwardly beyond the inner diameter of said glass tube.

21. An arrangement according to claim 19, said shoulder stop extending radially inwardly no further than the effective inner diameter of said tube.

22. An arrangement according to claim 21,
said laterally extending finger-grip protrusion having a smoothly arcuate fillet forming a forward connecting zone with the tube-engaging sheath section of said finger-grip sleeve at the outer end of said finger-grip sleeve lying over and in lateral alignment with said fire-polished beaded one end of said tube.

23. An arrangement according to claim 22,
said laterally extending finger-grip protrusion comprising a laterally extending flange,
said laterally extending flange being annular in extent and disposed axially beyond the respective end of said tube, and a smoothly enlarged annular fillet formed at the annular juncture zone between the longitudinally tubular portion of said finger-grip sleeve and said annular flange, said enlarged annular fillet laterally overlying and encompassing the respective annular beaded end of said tube.

24. A glass tube and non-glass finger grip and nose-forming arrangement for use particularly in packaging and subsequent dispensing of chemicals, comprising
a substantially cylindrical glass tube having fire-polished beaded opposite ends,
a finger-grip sleeve of thermoplastic resin and having a tube-gripping sheath section laterally extending finger-grip protrusion integrally formed thereon,
and a nose-forming sleeve of thermoplastic resin and having a reduced diameter section integral with a tube-gripping sheath section thereof,
said sleeves being stretch-fit along their sheath sections over and onto respectively opposite ends of said glass tube,
a piston slidably disposed in sealing relation within and at said end of said glass tube having said finger-grip sleeve thereon,
a valve seal disposed at the opposite nose end of said glass tube,
and a dispensable liquid contained within said tube between said piston and said valve seal,
said laterally extending finger-grip protrusion having an enlarged annular fillet juncture with the longitudinally extending tube-engaging portion of said finger-grip sleeve and lying over and in lateral alignment with said fire-polished beaded one end of said tube,
said laterally extending finger-grip protrusion comprising a laterally extending flange,
said laterally extending flange being annular in extent and having a main forward surface disposed longitudinally facing an imaginary plane extending across the end face of the respective annular fire-polished beaded end of said tube.

25. A glass tube and non-glass finger grip and nose-forming arrangement for use particularly in packaging and subsequent dispensing of chemicals, comprising
a substantially cylindrical glass tube having fire-polished beaded opposite ends,
a finger-grip sleeve of thermoplastic resin and having a tube-gripping sheath section laterally extending finger-grip protrusion integrally formed thereon,
and a nose-forming sleeve of thermoplastic resin and having a reduced diameter section integral with a tube-gripping sheath section thereof,
said sleeves being stretch-fit along their sheath sections over and onto respectively opposite ends of said glass tube,
a piston slidably disposed in sealing relation within and at said end of said glass tube having said finger-grip sleeve thereon,
a valve seal disposed at the opposite nose end of said glass tube,
and a dispensable liquid contained within said tube between said piston and said valve seal,
both of said sleeve sheaths having a laterally outwardly extending annular enlargement section at and in substantial lateral encompassing relation with the respective annular fire-polished end bead on said glass tube.

26. A glass tube and non-glass finger grip and nose-forming arrangement for use particularly in packaging and subsequent dispensing of chemicals, comprising
a substantially cylindrical glass tube,
a finger-grip sleeve of thermoplastic resin and having a tube-gripping sheath section laterally extending finger-grip protrusion integrally formed thereon,
and a nose-forming sleeve of thermoplastic resin and having a reduced diameter section integral with a tube-gripping sheath section thereof,
said sleeves being stretch-fit along their sheath sections over and onto respectively opposite ends of said glass tube,
a piston slidably disposed in sealing relation within and at said end of said glass tube having said finger-grip sleeve thereon,
a valve seal disposed at the opposite nose end of said glass tube,
and a dispensable liquid contained within said tube between said piston and said valve seal,
said sleeves being fitted onto said glass tube while said sleeves are at an elevated stress-relieving temperature substantially higher than the temperature of said glass tube and any material contained therein.

27. A dispenser arrangement comprising
a barrel section having a straight cylindrical bore with a liquid containment and plunger-guiding midsection and an open forward discharge end section which is contiguous to and forms an extension of said midsection, said bore being of substantially constant diameter along its effective liquid-containment and plunger-guiding midsection and its contiguous forward discharge end section,
a slidable pop-out valve plug having a section of soft elastic material disposed in radially elastically compressed sealing condition in and across said forward end of said tube bore,
and a nose section disposed at and connecting with said forward discharge end and having a forward end wall with a reduced diameter dispensing orifice formed therein,
said nose section forming a fluid flow by-pass cavity between the respective forward end of said tube barrel section and said reduced diameter dispensing portion of said nose section, said by-pass cavity being of greater effective size than the relaxed size of said pop-out valve plug at all corresponding annular and longitudinal points along the length and annular periphery of said plug and said cavity to enable free plug movement within said cavity and fluid by-pass flow around the annular periphery of said pop-out valve plug when such plug is longitudinally popped out into said by-pass cavity by forward motion of said plunger.

28. A dispenser according to claim 27,
said barrel section being a cylindrical tube of substantially constant internal diameter along its effective bore length and said nose section being a separate element having an internal diameter larger than said diameter of said cylindrical tube and forming said by-pass cavity.

29. A dispenser according to claim 28,
and a longitudinally manually movable plunger seal slidably disposed in said substantially constant diameter bore rearwardly of said pop-out valve plug.

30. A dispenser according to claim 29,
said cylindrical tube barrel section comprising a substantially cylindrical glass tube formed of a length of substantially constant diameter thin-walled glass tubing of substantially constant wall thickness along its length and having a wall thickness substantially smaller than the outer and inner wall diameters of said glass tubing,
said nose section comprising a plastic sleeve sheath secured about the forward end of said glass tubing.

31. A dispenser according to claim 30,
said plastic sleeve sheath engaging said forward end of said glass tubing in a stretch fit and having a substantially constant circumferential interior extending beyond the end of said glass tubing and forming the circumferential bounding wall of said by-pass cavity.

32. A dispenser according to claim 30,
said plastic sleeve sheath being cam stretch fit over said forward end of said glass tubing.

33. A dispenser according to claim 32,
and a sloped annular cam surface formed on one of the longitudinally inner end of said nose-forming sheath and the respective forward end of said glass tubing.

34. A dispenser according to claim 33,
said sloped annular cam surface being formed on said forward end of said glass tubing.

35. A dispenser according to claim 33,
said sloped annular cam surface being an annular bevel.

36. A dispenser according to claim 33,
said sloped annular cam surface being smoothly arcuate in longitudinal section.

37. A dispenser according to claim 36,
said sloped annular cam surface being formed by and as a part of an annular fire-polished rim formed on said forward end of said glass tubing.

38. A dispenser according to claim 37,
said annular fire-polished rim comprising a fire-polished raised annular bead.

39. A dispenser according to claim 38,
a said sloped annular cam surface being formed on both said glass tubing and the longitudinally inner end of said sleeve.

40. A dispenser according to claim 30,
said nose sleeve sheath being formed of polypropylene.

41. A dispenser according to claim 30,
and a finger-gripping plastic sleeve sheath secured about the rear of said glass tubing.

42. A dispenser according to claim 27,
and a longitudinally manually movable plunger seal slidably disposed in said substantially constant diameter bore rearwardly of said pop-out valve plug.

43. A dispenser according to claim 27,
said barrel section comprising a glass tube formed of a length of die-formed cylindrical glass tubing of substantially constant diameter along its length and of substantially constant wall thickness along its length, said wall thickness being substantially smaller than the inner and outer wall diameters of said glass tubing,
said nose section comprising a plastic sleeve sheath secured in annular frictional fit about the forward end of said glass tubing.

44. A dispenser according to claim 43,
said plastic sleeve sheath engaging said forward end of said glass tubing in a stretch fit.

45. A dispenser according to claim 43,
said plastic sleeve sheath being cam stretch fit over said forward end of said glass tubing.

46. A dispenser according to claim 45,
and a sloped annular cam surface formed on one of the longitudinally inner end of said nose sheath and the respective forward end of said glass tubing.

47. A dispenser according to claim 46,
said sloped annular cam surface being formed on said forward end of said glass tubing.

48. A dispenser according to claim 46,
said sloped annular cam surface being an annular bevel.

49. A dispenser according to claim 46,
said sloped annular cam surface being smoothly arcuate in longitudinal section.

50. A dispenser according to claim 49,
said sloped annular cam surface being formed by and as a part of an annular fire-polished rim formed on said forward end of said glass tubing.

51. A dispenser according to claim 50,
said annular fire-polished rim comprising a fire-polished raised annular bead.

52. A dispenser according to claim 51,
a said sloped annular cam surface being formed on both said glass tubing and the longitudinally inner end of said sleeve.

53. A dispenser according to claim 27,
said fluid by-pass cavity being substantially cylindrical and having a circumferentially oversized interior relative to said plug, along a length greater than the length of said plug.

54. A dispenser according to claim 27,
said oversized interior of said cavity being substantially cylindrical along a length thereof.

55. A dispenser according to claim 54,
said oversized interior of said cavity being substantially cylindrical along its length.

56. A dispenser according to claim 27,
said fluid by-pass cavity being substantially cylindrical and having a circumferentially oversized interior relative to said plug, along a length greater than the length of said plug.

57. A dispenser according to claim 27,
said fluid by-pass cavity having an oversized interior relative to said plug, along a length thereof greater than the effective sealing length of said plug.

* * * * *